United States Patent [19]

Luken et al.

[11] Patent Number: 5,569,802
[45] Date of Patent: Oct. 29, 1996

[54] CATALYST, PROCESS FOR THE PREPARATION THEREOF AND PROCESS FOR THE SELECTIVE HYDROGENATION OF UNSATURATED COMPOUNDS

[75] Inventors: Hans-Gerd Lüken; Lothar Fischer; Wilhelm Droste; Bernd Nowitzki, all of Marl, Germany

[73] Assignee: Huels Aktiengesellschaft, Marl, Germany

[21] Appl. No.: 313,835

[22] Filed: Sep. 28, 1994

Related U.S. Application Data

[62] Division of Ser. No. 82,450, Jun. 25, 1993, abandoned.

[30] Foreign Application Priority Data

Jun. 27, 1992 [DE] Germany ............... 42 21 139.5

[51] Int. Cl.⁶ .................. C07C 5/00; C07C 5/03; C07C 5/05

[52] U.S. Cl. ............... 585/269; 585/266; 585/271; 585/272

[58] Field of Search ................. 585/266, 269, 585/271, 272

[56] References Cited

U.S. PATENT DOCUMENTS 3,944,627  3/1976  Schram et al. ............... 260/668 R
4,075,254  2/1978  Boodman et al. ............. 260/667

*Primary Examiner*—Glenn A. Caldarola
*Assistant Examiner*—E. D. Irzinski
*Attorney, Agent, or Firm*—Oblon, Spivak, McClelland, Maier & Neustadt, P.C.

[57] ABSTRACT

The present invention relates to a catalyst for the selective hydrogenation of an unsaturated compound, based on a noble metal and/or a noble-metal oxide on an aluminum oxide support, and to a process for the preparation of the catalyst. The present invention further relates to a process for the selective hydrogenation of unsaturated compounds.

8 Claims, 1 Drawing Sheet

CATALYST, PROCESS FOR THE PREPARATION THEREOF AND PROCESS FOR THE SELECTIVE HYDROGENATION OF UNSATURATED COMPOUNDS

This is a division of application Ser. No. 08/082,450, filed on Jun. 25, 1993, and now abandoned.

BACKGROUND OF THE INVENTION

1. Field of the Invention

The present invention relates to a catalyst based on a noble metal and/or a noble-metal oxide on an aluminum oxide support for the selective hydrogenation of an unsaturated compound, to a process for the preparation of the catalyst and to a process for the selective hydrogenation of unsaturated compounds.

2. Discussion of the Background

Selective hydrogenations on catalysts are well-known in the chemical industry and in the oil-processing industry, where they can have various applications. For example, a selective hydrogenation can be carried out in order to free certain products, such as, for example, ethene or propene, from undesired by-products, such as diolefins and acetylenes, which would interfere with further processing of the olefins. Another application may be the selective hydrogenation of substances which form during a reaction and, as undesired by-products, cause a reduction in the overall yield of the target products. Selective hydrogenation can be used, if desired, to convert such byproducts back into starting materials, which can then be recycled into the process.

A typical example of the latter application is the selective hydrogenation of $\alpha$-methylstyrene to cumene in processes for the preparation of phenol and acetone, for example in the Hock phenol synthesis (see Weissermel/Arpe, Industrielle Organische Chemie [Industrial Organic Chemistry], Verlag Chemie, 1976, pp. 291 ff.). A by-product obtained in the phenol synthesis is $\alpha$-methylstyrene. Selective hydrogenation of the $\alpha$-methylstyrene to cumene gives fresh starting material, which, if recycled into the process, ultimately results in improved efficiency of the process.

One of the crucial factors for selective hydrogenation is the initial selectivity of the catalyst employed. If an excessive amount of by-product(s) is formed at the beginning of the selective hydrogenation (for example, due to undesired total hydrogenation), a prolonged start-up procedure for the hydrogenation plant and a decrease in the yield of the process arise, resulting in a reduction in overall efficiency.

DE-A 2,758,318 discloses a process for the selective hydrogenation of unsaturated compounds in which the hydrogenation catalyst is brought into contact with, inter alia, the components to be hydrogenated for an appropriate length of time in the absence of hydrogen.

DE-A 2,758,274 discloses that the hydrogenation selectivity of a hydrogenation catalyst can be increased by treating the hydrogenation catalyst with gaseous ammonia for a sufficient length of time and subsequently carrying out the selective catalytic hydrogenation of the unsaturated compounds with hydrogen.

The catalysts used are, in particular, noble metals, such as ruthenium, rhodium, palladium or platinum, on supports. Examples of suitable supports are clays, magnesium oxide, gels of silicon dioxide and aluminum oxide, zeolites, activated charcoal and activated aluminum oxide, which may each be in various forms, such as pellets, beads, etc.

Both of the above processes are complex and result in increased operating costs due to the complicated start-up procedures necessary for the catalyst.

SUMMARY OF THE INVENTION

Accordingly, one object of the present invention is to provide a novel catalyst which has high initial selectivity in the hydrogenation of unsaturated compounds.

A further object of the present invention is to provide a novel catalyst which facilitates immediate, full use in processes for the selective hydrogenation of unsaturated compounds.

A further object of the present invention is to provide a novel process for preparing a catalyst which has high initial selectivity and which facilitates immediate, full use in processes for the hydrogenation of unsaturated compounds.

A further object of the present invention is to provide a novel process for the selective hydrogenation of unsaturated compounds exhibiting improved selectivity, yields and/or efficiency.

It has now been found, surprisingly, that a catalyst based on a noble metal and/or a noble-metal oxide on an aluminum oxide support has very high initial selectivity, and can thus be employed immediately and fully for the selective hydrogenation of unsaturated compounds, if the fresh catalyst has the following X-ray diffraction pattern:

| d $[10^{-10}$ m] | I/Io |
|---|---|
| 4.51 | 5–10 |
| 2.76 | 15–40 |
| 2.64 | |
| 2.37 | 40–45 |
| 2.27 | 25–35 |
| 2.15 | up to 15 |
| 1.97 | 55–70 |
| 1.66 | up to 15 |
| 1.52 | 15–30 |
| 1.39 | 100 |
| 1.31 | up to 15 |

With the aid of the present catalyst, prolonged and high-cost start-up procedures can be avoided.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
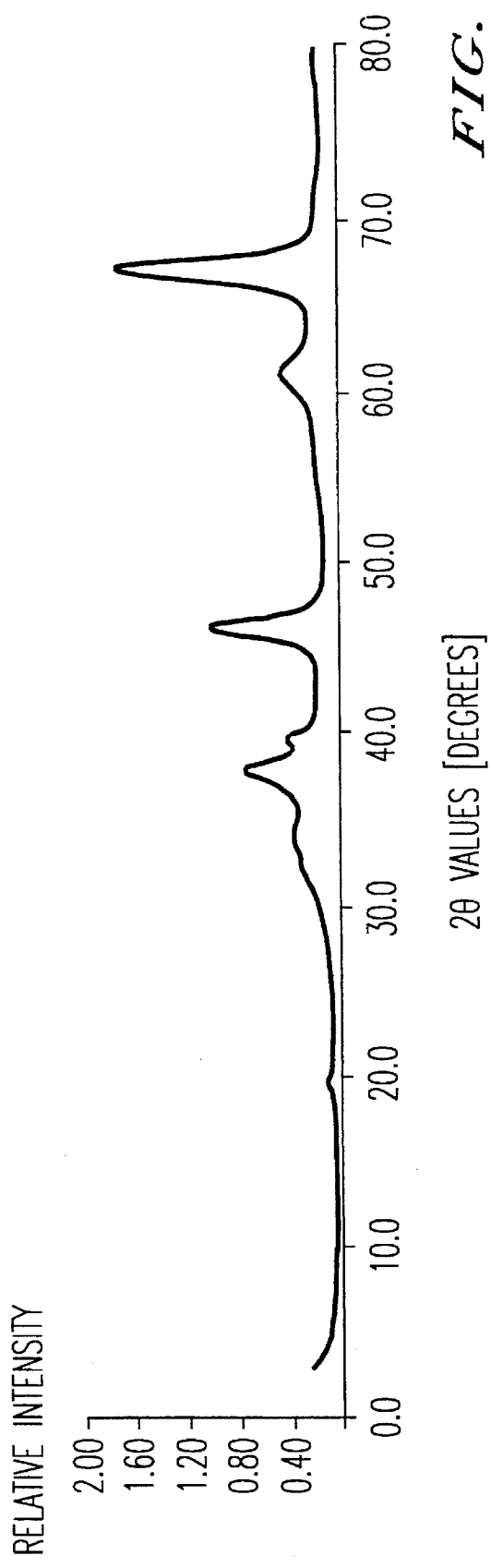
FIG. 1 shows the X-ray diffraction diagram (Cu $K\overline{\alpha}$) of a first embodiment of the present catalyst (see Example 1 infra)

The present invention therefore relates to a catalyst for selective hydrogenation of unsaturated compounds, based on a noble metal and/or a noble-metal oxide on an aluminum oxide support, wherein the fresh catalyst has the following X-ray diffraction pattern:

| d [$10^{-10}$ m] | I/Io |
|---|---|
| 4.51 | 5–10 |
| 2.76 | 15–40 |
| 2.64 | |
| 2.37 | 40–45 |
| 2.27 | 25–35 |
| 2.15 | up to 15 |
| 1.97 | 55–70 |
| 1.66 | up to 15 |
| 1.52 | 15–30 |
| 1.39 | 100 |
| 1.31 | up to 15 |

The term "d" denotes the interplanar spacing, and the term "I/Io" denotes the relative intensities of the X-ray reflections.

The present invention furthermore relates to a process for the preparation of a catalyst for the selective hydrogenation unsaturated compounds, wherein a noble metal is introduced into an aluminum oxide support in the form of an aqueous noble-metal salt solution.

Suitable support materials for the present catalyst are various aluminum oxide phases. The aluminum oxide support preferably contains η-aluminum oxide and/or γ-aluminum oxide.

The aluminum oxide support which has been treated with an aqueous noble-metal salt solution is preferably dried at a temperature of from 50° to 200° C. until sufficiently dry to conduct subsequent processing, and preferably for a length of time of from 2 to 20 hours. The dried support is subsequently heated at a temperature of from 250° to 650° C. for a length of time of from 4 to 48 hours.

The present invention also relates to a process for the selective hydrogenation of unsaturated compounds, employing a catalyst in which a noble metal is introduced into an aluminum oxide support in the form of an aqueous noble-metal salt solution.

The present catalyst preferably contains palladium, palladium oxide, or a mixture thereof; i.e., the present catalyst preferably has the formula $PdO_x$, where x=0 to 1. The present catalyst may also contain, in addition to palladium and/or palladium oxide, noble metals selected from the group consisting of platinum, iridium, ruthenium, rhodium and mixtures thereof, as well as the corresponding oxides of these noble metals.

The content of noble metal and/or noble-metal oxides in the present catalyst is preferably from 0.01 to 3% by weight of the total weight of the catalyst, particularly preferably from 0.1 to 1% by weight of the total weight of the catalyst.

In principle, the present catalyst can contain any or all noble metals which are conventionally used in hydrogenation catalysts. Thus, the present invention also encompasses a method for the selective hydrogenation of one or more unsaturated compounds, the improvement comprising contacting the unsaturated compound(s) with a catalyst prepared by a process comprising contacting an aluminum oxide support with a noble metal salt solution to form an impregnated aluminum oxide, drying the impregnated aluminum oxide, and heating said dried impregnated aluminum oxide to form said catalyst.

The noble metals and/or noble-metal oxides are preferably located in an outer peripheral zone of the present catalyst. The phrase "outer peripheral zone" refers to the material at and/or near the surface of the catalyst, up to a depth of from 5 to 200 μm, particularly preferably of from 30 to 100 μm, from the surface of the catalyst particles.

The primary crystallites present in the fresh catalyst preferably have a size of from 0.1 to 30 nm, particularly preferably a size of from 1 to 15 nm. "Fresh catalyst" refers to the catalyst after it has been prepared, prior to its first use in a selective hydrogenation process.

In addition, the fresh catalyst may contain other substances, such as alkali metal and/or alkaline earth metal compounds (for example, oxides of lithium, potassium, ruthenium, magnesium, calcium, and mixtures thereof), nitrates, carbonates, phosphates and sulphates of one or more alkali metals and/or alkaline earth metals, silicon oxides and iron oxides, etc. The content of sodium in the fresh catalyst can be from 0.001 to 3% by weight of the catalyst, preferably from 0.01 to 1% by weight. Substances other than sodium may each be present in an amount of ≦1% by weight of the total weight of the catalyst.

The total BET surface area of the fresh catalyst is preferably between 50 and 250 m²/g of fresh catalyst, in particular between 100 and 180 m²/g of fresh catalyst. The pore volume of the fresh catalyst is preferably from 0.2 to 0.8 ml/g of fresh catalyst, in particular from 0.3 to 0.6 ml/g of fresh catalyst. The pore size of the fresh catalyst is preferably from 3 to 30 nm, in particular from 4 to 20 nm.

In the present application, an "unsaturated" compound refers to an aromatic compound having a substituent containing an ethylenically unsaturated carbon-carbon double bond. "Selective" hydrogenation refers to the selective addition of dihydrogen to an ethylenically unsaturated carbon-carbon double bond in an "unsaturated" compound, without significant addition of dihydrogen to the aromatic ring. In other words, for example, "selective" hydrogenation avoids converting a phenyl radical to a cyclohexadienyl, cyclohexenyl, and/or cyclohexyl radical.

The selective hydrogenation of one or more unsaturated compounds with the aid of the present catalyst is preferably carried out at a pressure of from 2 to 30 bar absolute and at a temperature of from 40° to 180° C. It is appropriate to introduce or use amounts of hydrogen and of unsaturated compound(s), such that the molar ratio of hydrogen to unsaturated compound(s) is from 1:1 to 3:1.

The present selective hydrogenation process is particularly suitable for styrene and alkylated vinylbenzenes of from 9 to 20 carbon atoms, preferably of from 9 to 15 carbon atoms. More preferred unsaturated compound(s) suitable for the present process include α-methylstyrene, β-methylstyrene, o-vinyltoluene, m-vinyltoluene and p-vinyltoluene, and most preferably, α-methylstyrene.

In the preparation of the present catalyst, the aluminum oxide precursor compounds for the aluminum oxide support can be, for example, bayerite and/or pseudo-boehmite. The aluminum oxide precursor compounds can be treated with an acid, preferably with nitric acid. The phrase "treated with an acid" refers to kneading the precursor compounds in a kneader, and successively adding acid to the kneader. After acid treatment, the precursor compounds are subsequently shaped into a molding by a conventional process. The resultant moldings can then be dried, for example at a temperature of from 80° to 140° C. for a length of time of from 2 to 20 hours, or until sufficiently dry to conduct further processing steps, and then calcined or heated at a temperature of from 400° to 700° C. for a length of time sufficient to provide an aluminum oxide support which can be impregnated with an aqueous noble metal salt solution.

An aluminum oxide support prepared in this way can then be impregnated with an aqueous noble-metal salt solution. The impregnation of the aluminum oxide support can be carried out by contacting the aluminum oxide support with the aqueous noble-metal salt solution at a temperature of from room temperature (about 15° C.) to 100° C. The impregnated aluminum oxide support is then preferably dried at a temperature of from 50° to 200° C. for a length of time of from 2 to 20 hours, and subsequently heated at a temperature of from 250° to 650° C. for a length of time of from 4 to 48 hours.

A novel catalyst prepared in this way can be employed directly for selective hydrogenation.

Other features of the invention will become apparent in the course of the following descriptions of exemplary embodiments which are given for illustration of the invention and are not intended to be limiting thereof.

EXAMPLE 1

The conversion of α-methylstyrene into cumene was used as an example of a selective hydrogenation. An undesired by-product which may be formed in the conversion of α-methylstyrene into cumene is the ring-hydrogenated product isopropylcyclohexane. The formation of isopropylcyclohexane has a considerable adverse effect on the reaction, and thus, on the yield of cumene.

The novel catalyst 1 was prepared as follows:

Bayerite, the aluminum oxide precursor compound used for the aluminum oxide support, was treated with nitric acid in a mixer, and was subsequently shaped by a conventional process to form a molding. The molding was then dried at a temperature of from 120° C. for 18 hours and calcined at a temperature of 650° C. for 16 hours.

The resultant aluminum oxide support was impregnated with an aqueous palladium(II) nitrate solution, wherein the temperature of the aluminum oxide support and the solution was at ambient temperature. The solution volume was approximately 80% of the total pore volume of the aluminum oxide support. The impregnated aluminum oxide support was then dried at a temperature of 110° C. for 16 hours and subsequently calcined at a temperature of 450° C. for 16 hours. The resultant catalyst 1 contained 0.5% by weight of palladium and palladium oxide, calculated as Pd. FIG. 1 shows the X-ray diffraction diagram (Cu K$\overline{\alpha}$) of the catalyst 1. The relative intensities are plotted as a function of the diffraction angle, shown in 2Θ values (degrees).

20 g of the catalyst 1 were introduced into a liquid-phase circulation apparatus comprising a reactor, heat exchanger, separator and pump. The liquid-phase circulation apparatus was filled with 1000 cm$^3$ of technical-grade, liquid starting material of the composition listed in Table 1. The apparatus was sealed, flushed with nitrogen and heated to a reaction temperature of 70° C. The starting material was subsequently hydrogenated at a hydrogen pressure of 8 bar abs. for 3 hours.

The chemical compositions of the starting material and of the hydrogenation product are shown in Table 1 below. The residual content of α-methylstyrene in the hydrogenation product was less than 10 ppm by weight (see Table 1). The content of isopropylcyclohexane increased by only 90 ppm by weight.

TABLE 1

|  | Starting Material (% by weight) | Hydrogenation Product (% by weight) |
| --- | --- | --- |
| Cumene | 73.3 | 91.2 |
| α-Methylstyrene | 18.1 | <0.001 |
| Isopropylcyclohexane | 0.005 | 0.014 |

EXAMPLE 2

The novel catalyst 2 was prepared as follows:

The aluminum oxide precursor compound used for the aluminum oxide support was pseudo-boehmite, which was treated with nitric acid in a compounder and subsequently shaped by the same process as example 1 to prepare a molding. The molding was then dried at a temperature of 120° C. for 16 hours and calcined at a temperature of 550° C. for 20 hours.

Figure 2:
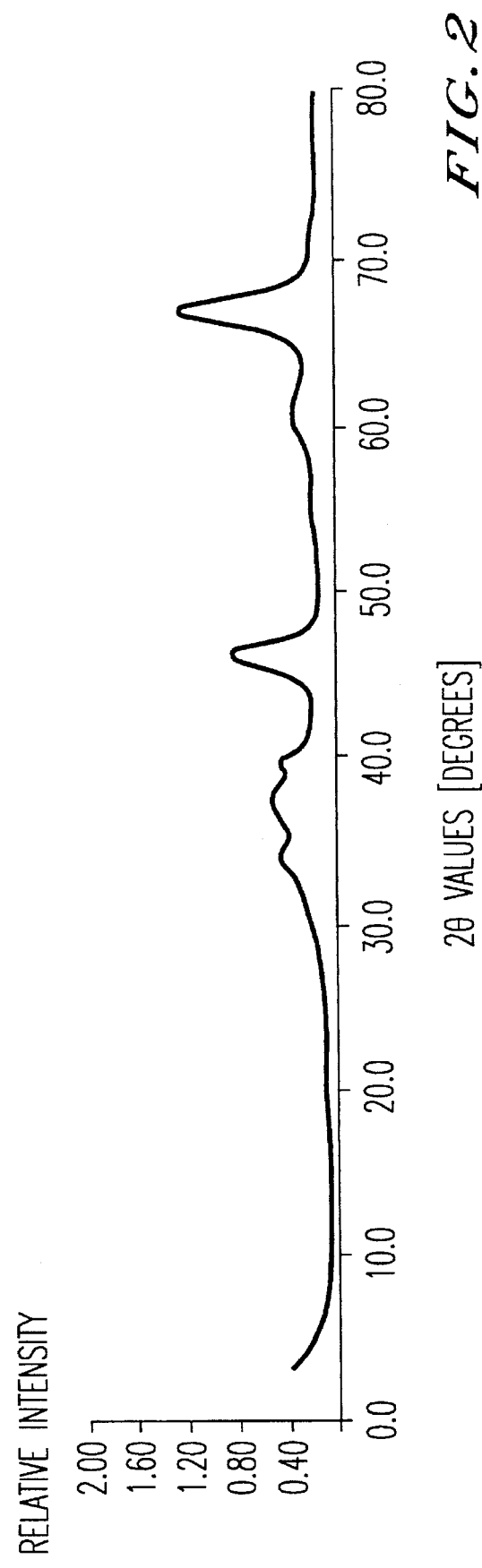
FIG. 2 shows the X-ray diffraction diagram (Cu $K\overline{\alpha}$) of a second embodiment of the present catalyst (See Example 2 infra).

The resultant aluminum oxide support was impregnated with an aqueous palladium(II) nitrate solution, the temperature of the aluminum oxide support being 95°–100° C. and the aqueous solution was at ambient temperature. The solution volume was 80% of the total pore volume of the support. The impregnated aluminum oxide support was then dried at a temperature of 130° C. for 16 hours and subsequently calcined at a temperature of 450° C. for 16 hours. The resultant catalyst 2 contained 1% by weight of palladium and palladium oxide, calculated as Pd. FIG. 2 shows the X-ray diffraction diagram (Cu K$\overline{\alpha}$) of the catalyst 2. The relative intensities are plotted as a function of the diffraction angle, shown in 2Θ values (degrees).

The starting material as shown in Table 2 (see below) was hydrogenated as in Example 1 with the aid of catalyst 2, but the reaction temperature was 110° C. The chemical compositions of the starting material and of the hydrogenation product are shown in Table 2 below.

TABLE 2

|  | Starting Material (% by weight) | Hydrogenation Product (% by weight) |
| --- | --- | --- |
| Cumene | 73.6 | 91.6 |
| α-Methylstyrene | 18.0 | 0.029 |
| Isopropylcyclohexane | 0.005 | 0.016 |

After a reaction time of two hours, the α-methylstyrene content in the hydrogenation product was no more than 0.029% by weight. The content of isopropylcyclohexane had risen by only 110 ppm by weight.

EXAMPLE 3

The selective hydrogenation was carried out as described in Example 1, but the reaction temperature was 130° C. The hydrogenation catalyst used was catalyst 1 from Example 1. Starting from 18% by weight of α-methylstyrene in the starting material, the residual content after a reaction time of 2 hours was less than 10 ppm by weight of α-methylstyrene in the hydrogenation product. The content of isopropylcyclohexane had risen by only 160 ppm by weight.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for selectively hydrogenating an ethylenically unsaturated carbon-carbon double bond of an aromatic compound containing the same, which process comprises:

contacting a feedstock containing an aromatic compound having a substituent containing an ethylenically unsaturated carbon-carbon double bond with a catalyst in the presence of hydrogen, said catalyst comprising (i) an aluminum oxide support, and (ii) one or more noble metals or noble metal oxides or both, under conditions effective for hydrogenating said ethylenically unsaturated carbon-carbon double bond of said aromatic compound, said catalyst having the following X-ray defraction pattern prior to its initial use:

| $d[10^{-10} \text{ m}]$ | $I/I_o$ |
| --- | --- |
| 4.51 | 5–10 |
| 2.76 | 15–40 |
| 2.64 | |
| 2.37 | 40–45 |
| 2.27 | 25–35 |
| 2.15 | up to 15 |
| 1.97 | 55–70 |
| 1.66 | up to 15 |
| 1.52 | 15–30 |
| 1.39 | 100 |
| 1.31 | up to 15. |

2. The process of claim 1, wherein said aromatic compound containing said ethylenically unsaturated carbon-carbon double bond is selected from the group consisting of α-methylstyrene, β-methylstyrene, o-vinyltoluene, m-vinyltoluene and p-vinyltoluene.

3. The process of claim 1, wherein said aluminum oxide support comprises η-aluminum oxide or γ-aluminum oxide or a mixture thereof.

4. The process of claim 1, wherein in said catalyst, the one or more noble metals or noble metal oxides or both are located at or near the surface of the catalyst up to a depth of from 5 to 200 μm.

5. The process of claim 1, wherein said one or more noble metals or noble metal oxides or both comprises from 0.01 to 3% by weight of the total weight of the catalyst.

6. The process of claim 1, wherein said catalyst contains primary crystallites having a size of from 0.1 to 30 nm.

7. The process of claim 1, wherein said catalyst has a total BET surface area of between 50 and 250 m²/g when fresh.

8. The process of claim 1, wherein said catalyst has a pore size when fresh of from 3 to 30 nm.

* * * * *